US00PP11137P

United States Patent [19]

Bergman

[11] Patent Number: Plant 11,137

[45] Date of Patent: Nov. 30, 1999

[54] AZALEA PLANT NAMED 'LAVENDER LACE'

[75] Inventor: Wendy R. Bergman, Lehigh Acres, Fla.

[73] Assignee: Yoder Brothers, Inc., Barberton, Ohio

[21] Appl. No.: 09/082,074

[22] Filed: May 20, 1998

[51] Int. Cl.[6] ..... A01H 5/00

[52] U.S. Cl. ..... Plt./238

[58] Field of Search ..... Plt./238, 239, 240

[56] References Cited

U.S. PATENT DOCUMENTS

P.P. 10,508 7/1998 Stahnke ..... Plt./238

*Primary Examiner*—Howard J. Locker

*Assistant Examiner*—Kent L. Bell

*Attorney, Agent, or Firm*—C. A. Whealy

[57] ABSTRACT

A new and distinct cultivar of Azalea plant named 'Lavender Lace', characterized by its large, vigorous and dense plants that are very freely branching; very uniform symmetrical and mostly upright plant habit; uniform flowering numerous, large, showy, ruffled, single flowers; lavender-colored flowers that resist fading; and excellent postproduction longevity with plants maintaining good flower substance for about four weeks in an interior environment.

1 Drawing Sheet

BACKGROUND OF THE INVENTION

The present invention relates to a new and distinct cultivar of Azalea, botanically known as *Rhododendron hybrida,* an evergreen greenhouse-forcing type, and hereinafter referred to by the name 'Lavender Lace'.

The new Azalea is a product of a planned breeding program conducted by the inventor in Alva, Fla. The objective of the breeding program is to create new Azalea varieties having uniform plant habit and uniform flowering, numerous flowers, good foliage retention during the cooling and forcing periods, and excellent postproduction longevity.

The new Azalea originated from a cross made by the inventor in Alva, Fla., of an unnamed selection of *Rhododendron mucronatum* as the female, or seed, parent with the proprietary *Rhododendron hybrida* breeding selection code number 0227 as the male, or pollen, parent.

Compared to plants of the female parent, an unnamed selection of *Rhododendron mucronatum,* plants of the new Azalea have a more uniform plant habit and darker, more intense flower color, and better flower color retention.

In addition to flower color and form, plants of the new Azalea are more uniform and symmetrical than plants of the coral double hose-in-hose-flowered proprietary selection code number 0227. Additionally, leaves of plants of the new Azalea are lighter in color and more pubescent than leaves of plants of the code number 0227.

The new Azalea was discovered and selected by the inventor as a flowering plant within the progeny of the stated cross in a controlled environment in Alva, Fla., on Jan., 1992. The selection of this plant was based on its desirable flower color, profust and uniform flowering, uniform plant habit and good postproduction longevity.

Asexual reproduction of the new Azalea by terminal cuttings taken in a controlled environment in Alva, Fla., has shown that the unique features of this new Azalea are stable and reproduced true to type in successive generations.

The new Azalea has not been observed under all possible environmental conditions. The phenotype may vary somewhat with variations in environment such as temperature, daylength, light intensity, nutrition and water status without, however, any variance in genotype.

BRIEF SUMMARY OF THE INVENTION

The following traits have been repeatedly observed and are determined to be the unique characteristics of 'Lavender Lace'. These characteristics in combination distinguish 'Lavender Lace' as a new and distinct cultivar:

1. Large, vigorous and dense plants that are very freely branching.

2. Very uniform, symmetrical and mostly upright plant habit.

3. Uniform flowering.

4. Numerous, large, showy, ruffled, single flowers.

5. Lavender-colored flowers that resist fading.

6. Excellent postproduction longevity with plants maintaining good flower substance for about four weeks in an interior environment.

Plants of the new Azalea can be compared to plants of the lavender-flowered cultivar 'Violacea' (not patented). However, in side-by-side comparisons conducted in Alva, Fla., plants of the new Azalea differ from plants of the cultivar 'Violacea' in the following characteristics:

1. Plants of the Azalea are much more vigorous than plants of the cultivar 'Violacea'.

2. Leaves of plants of the new Azalea are larger and lighter in color than leaves of plants of the cultivar 'Violacea'.

3. Flowers of plants of the new Azalea are single whereas flowers of plants of the cultivar 'Violacea' are double in form.

4. Flowers of plants of the new Azalea are much lighter in color than flowers of plants of the cultivar 'Violacea'.

BRIEF DESCRIPTION OF THE PHOTOGRAPHS

The accompanying colored photographs illustrate the overall appearance of the new Azalea, showing the colors as true as it is reasonably possible to obtain in colored reproductions of this type.

The photograph at the top of the sheet comprises a side perspective view of a typical plant of 'Lavender Lace'.

The photograph at the bottom of the sheet is a close-up view of typical flowers of 'Lavender Lace'. Flower and foliage colors in the photographs may appear different from the actual colors due to light reflectance.

DETAILED BOTANICAL DESCRIPTION

The aforementioned and following observations, measurements, values, and comparisons describe plants grown in Alva, Fla., in 12.5-cm containers with day temperatures ranging from 16 to 35° C. and night temperatures ranging from 10 to 24° C. Plants were grown under 50 percent polypropylene shade cloth reducing ambient light levels to about 4,000 to 5,000 footcandles. After flower bud development, plants were cooled at 3 to 5° C. for six weeks to break flower bud dormancy. Plants were subsequently forced into flower under commercial conditions in a polyethylene-covered greenhouse.

In the following description, color references are made to The Royal Horticultural Society Colour Chart except where general terms of ordinary dictionary significance are used.

Botanical classification:

*Botanical.*—*Rhododendron hybrida* 'Lavender Lace'. Commercial: Evergreen greenhouse-forcing type Azalea.

Parentage:

*Male or pollen parent.*—Proprietary *Rhododendron hybrida* breeding selection code number 0227.

*Female or seed parent.*—An unnamed selection of *Rhododendron mucronatum.*

Propagation:

*Type.*—By terminal cuttings.

*Time to initiate roots.*—Summer: About 35 days at temperatures of 24° C.

Winter: About 42 days at temperatures of 24° C.

*Time to developo roots.*—Summer: About 63 days at temperatures of 24° C. Winter: About 77 days at temperatures of 24° C.

*Rooting habit.*—Vigorous and finely-branched.

Plant description:

*Plant form and growth habit.*—Perennial, evergreen, large, mostly upright, somewhat outwardly spreading, inverted triangle, uniform and symmetrical plant habit. Vigorous. Numerous flowers per plant.

*Branching habit.*—Very freely branching usually about five lateral branches develop after removal of terminal apex. Plant height, soil level to top of flowers: About 33 cm. Plant diameter, area of spread: About 45 cm.

*Lateral branch description.*—Length: About 41 cm. Diameter: About 8 mm. Color: Immature: 144B/144C. Mature: Woody, lighter than 165A. Texture: Pubescent.

Foliage description:

*Arrangement.*—Alternate, single.

*Length.*—About 6.1 cm.

*Width.*—About 2.1 cm.

*Shape.*—Narrowly elliptic.

*Apex.*—Mucronate.

*Base.*—Cuneate.

*Margin.*—Entire.

*Texture.*—Leathery, pubescent on both surfaces.

*Color.*—Young foliage, upper surface: 147A. Young foliage, lower surface: 147B. Mature foliage, upper surface: Slightly darker than 147A. Mature foliage, lower surface: 147B.

*Petiole.*—Length: About 1 cm. Diameter: About 2 mm. Color: 144B/144C.

Flower description:

*Natural flowering season.*—Spring after sufficient cool period.

*Time to flower* (*forcing period*).—After about four to six weeks of cooling at 4 to 9° C. plants will typically require an additional three to five weeks to develop about 12 colored flower buds.

*Flower arrangement.*—Flowers arranged singly at terminals with usually about three flowers per apex. Flowers face upward and outward. Very freely flowering.

*Flower appearance.*—Very large showy star-shaped single flowers. Lavender petals with dark hot pink-speckled throat. Flowers persistent.

*Flower diameter.*—About 11.5 cm.

*Postproduction longevity.*—Under interior conditions, plants maintain good flower substance for about four weeks.

*Flower bud* (*just starting to show petal color*).—Rate of opening: About three days depending on temperatures. Length: About 1.9 cm. Diameter: About 5 mm. Shape: Narrowly ovoid. Color: 77A/80A.

*Petals.*—Appearance: Satiny, ruffled. Texture: Smooth. Arrangement: Large single flowers that occasionally have a few stamenoidal petaloids. Corolla consists of five fused petals. Shape: Spatulate with rounded apex. Margin: Entire with undulating edge which gives a ruffled appearance. Length: About 6.25 cm. Width: About 4.5 cm. Color: When opening, upper and lower surfaces: 80A. Fully opened, upper surface: Iridescent, 80A. Fully opened, lower surface: Iridescent, 80A/80B. Throat: 61B speckles on upper three petals.

*Sepals.*—Arrangement: Five sepals fused into a star-shaped calyx. Texture: Pubescent. Shape: Ovate with attenuate apex. Margin: Entire. Color, upper and lower surfaces: 144A.

*Peduncles.*—Length: About 2.2 cm. Diameter: About 2 mm. Angle: Upright. Strength: Flexible, strong. Texture: Pubescent. Color: 144B/144C.

*Reproductive organs.*—Androecium: Stamen number: Five to ten, occasionally petaloid. Anther shape: Oblong. Anther size: About 3 mm by 1 mm. Anther color: Purple. Amount of pollen: Abundant. Pollen color: Creamy white. Gynoecium: Stigma shape: Rounded. Stigma color: Close to 80C. Style length: About 3.8 cm. Style color: Light green to cream white. Ovary color: Light green, heavily whiskered.

Disease resistance: No known Azalea diseases observed to date on plants grown under commercial greenhouse conditions.

Seed production: Seed production has not been observed.

It is claimed:

1. A new and distinct Azalea plant named 'Lavender Lace', as illustrated and described.

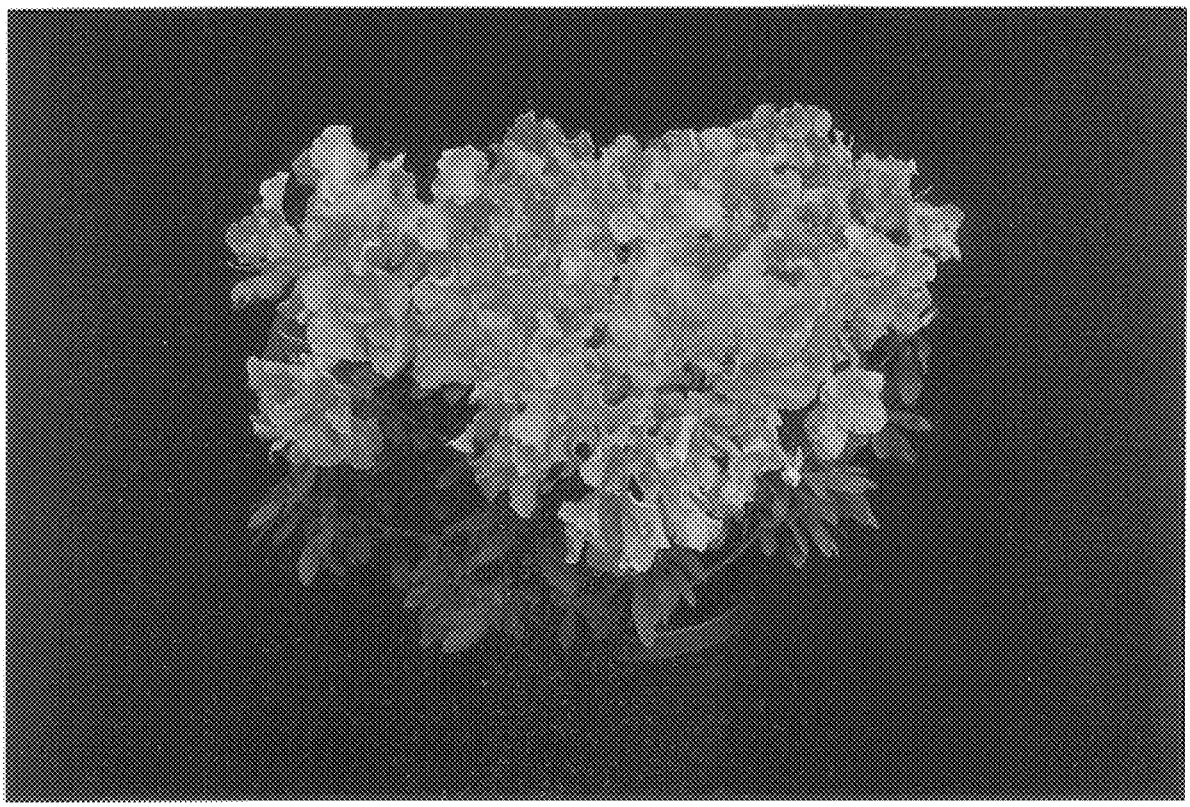
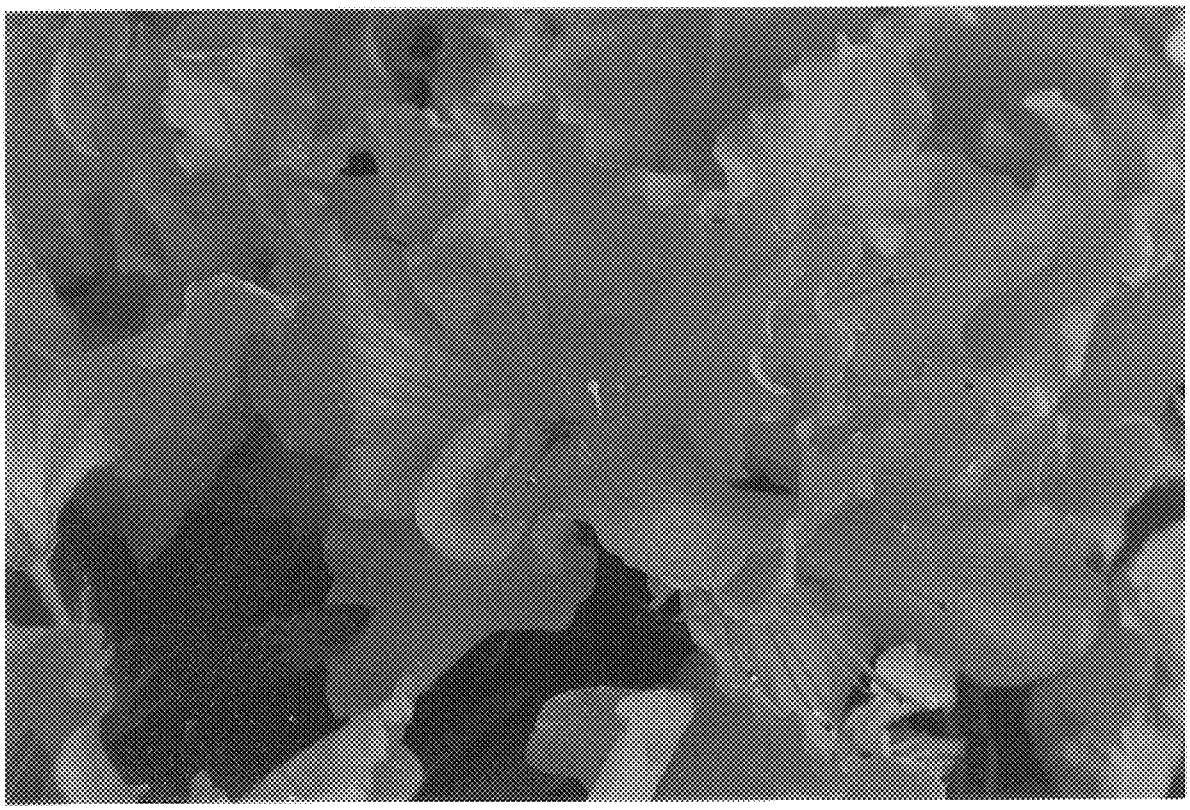

* * * * *